United States Patent [19]

Doring

[11] 4,409,994
[45] Oct. 18, 1983

[54] LAP JOINT MOLDING MEMBER FOR A PACEMAKER ELECTRODE LEAD

[75] Inventor: Carl Doring, Wollstonecraft, Australia

[73] Assignee: Telectronics Pty., Ltd., Lane Cove, Australia

[21] Appl. No.: 269,577

[22] Filed: Jun. 2, 1981

[51] Int. Cl.³ .............................................. A61N 1/04
[52] U.S. Cl. .................................. 128/785; 128/419 P
[58] Field of Search ...................... 128/419 P, 785, 786

[56] References Cited

U.S. PATENT DOCUMENTS

| 3,719,190 | 3/1973 | Avery | 128/418 |
|---|---|---|---|
| 4,033,357 | 7/1977 | Hellard et al. | 128/785 |
| 4,262,678 | 4/1981 | Stokes | 128/786 |
| 4,269,198 | 5/1981 | Stokes | 128/785 |
| 4,301,815 | 11/1981 | Doring | 128/786 |
| 4,317,459 | 3/1982 | Gilman | 128/785 |

FOREIGN PATENT DOCUMENTS

| 3948 | 9/1979 | European Pat. Off. |  |
| 5106 | 10/1979 | European Pat. Off. |  |
| 9619 | 4/1980 | European Pat. Off. |  |
| 41254 | 12/1981 | European Pat. Off. |  |
| 41791 | 12/1981 | European Pat. Off. |  |
| 43461 | 1/1982 | European Pat. Off. |  |
| WO79/05227 | 6/1979 | PCT Int'l Appl. | 128/786 |
| 1491942 | 11/1977 | United Kingdom. |  |
| 2015344 | 9/1979 | United Kingdom. |  |
| 1560411 | 2/1980 | United Kingdom. |  |
| 2067411 | 7/1981 | United Kingdom. |  |

*Primary Examiner*—Kyle L. Howell
*Assistant Examiner*—Max F. Hindenburg
*Attorney, Agent, or Firm*—Finnegan, Henderson, Farabow, Garrett & Dunner

[57] ABSTRACT

A cardiac pacemaker electrode lead comprising an electrode tip, an electrical conductor electrically coupled to the electrode tip, an insulative sheath covering a portion of the electrical conductor, and a molding member for covering the uninsulated portion of the electrical conductor and including a distal end for forming a first lap joint with the electrode tip and a proximal end for forming a second lap joint with the insulative sheath. Foldable tines are formed on the molding member and when unfolded extend at an angle from the molding member to anchor the electrode tip in trabecular muscles inside the heart. When folded, the tines are received in a recessed portion of the molding member such that the tines are substantially flush with the exterior surface of the lap joints.

19 Claims, 4 Drawing Figures

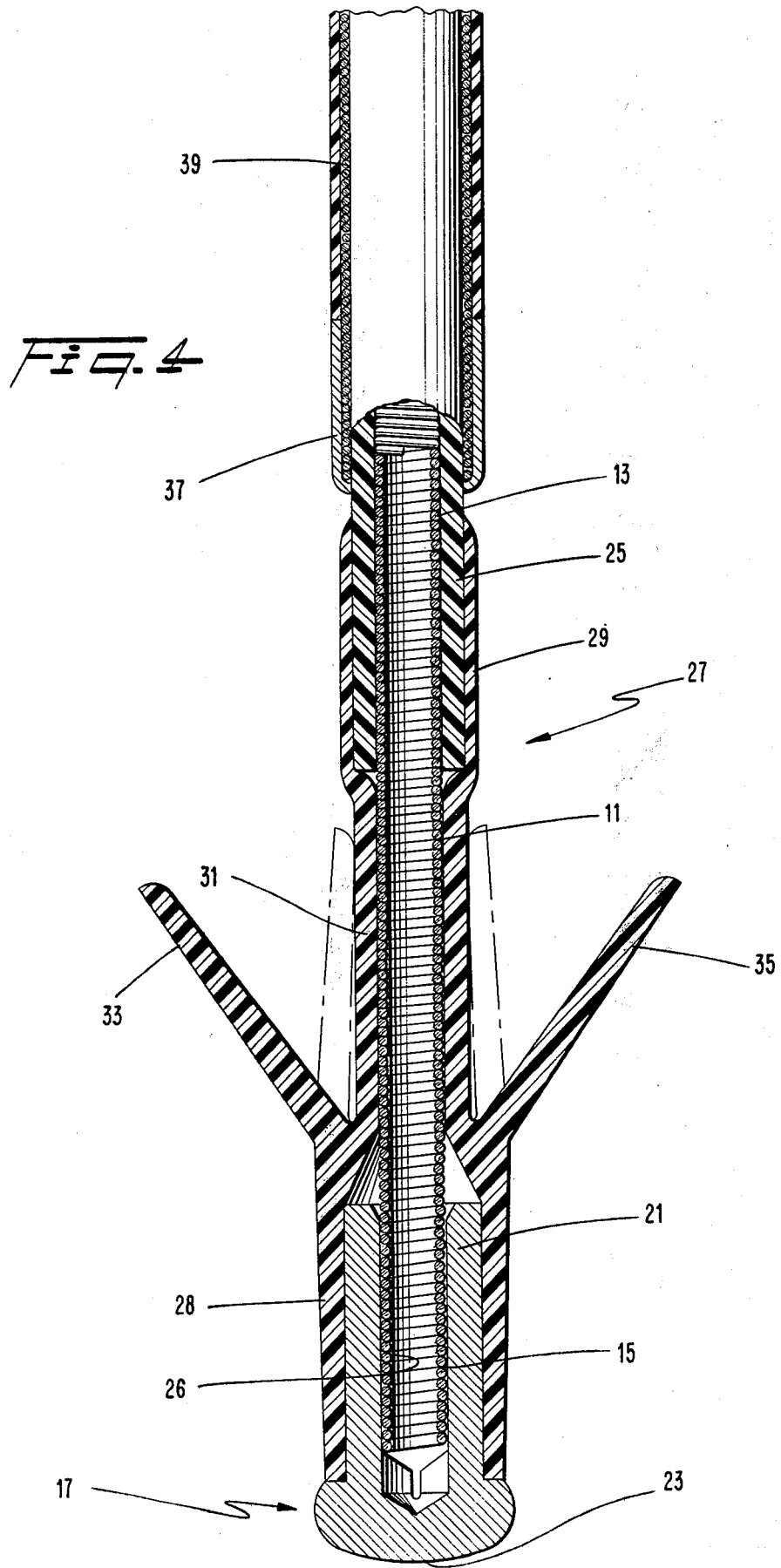

LAP JOINT MOLDING MEMBER FOR A PACEMAKER ELECTRODE LEAD

FIELD OF THE INVENTION

This invention relates with particularly to a tined electrode lead for use with a cardiac pacemaker.

BACKGROUND OF THE INVENTION

Recently, the implantation of sophisticated electronic devices has become a routine occurrence in many therapeutic procedures. Today many forms of medical electrode leads are available which are provided with a metallic distal electrode tip which is placed adjacent excitable tissue, such as the inside wall of the heart, whereby electric currents supplied to the distal tip stimulate the muscle in contact with the tip to initiate or to regulate heartbeats.

There are a number of conflicting design factors which must be resolved when determining the geometric shape of such medical electrode leads. For example, it is desirable to minimize the size of the electrode lead, and particularly the cross-sectional area, to facilitate the passage of the lead through tight places, such as the inside of small blood vessels, in order to reach desired locations. This aspect is particularly important where two leads are inserted through the same vein. Nevertheless, it is vitally important that the electrode lead have an effective anchoring configuration so that once the electrode tip is correctly positioned it remains in that position. Also, providing a smooth surface to minimize insertion and removal resistance lessens the danger of tissue damage and makes accurate location of the electrode tip possible.

As a solution to the need for an anchoring means, it has been proposed to form electrode tips including flanges or tines extending therefrom in order to engage body tissue such as the trabecular muscles inside the heart following insertion of the electrode tip. However, in striking a compromise between the need for anchoring and the need to minimize the resistance to insertion and removal of the electrode tip, some devices have exhibited an unsatisfactory anchoring effect because the size of the flange is restricted by the inside diameter of the smallest vein through which the flange must pass.

The devices that have employed flexible tines usually extend the tines at an acute angle with respect to the longitudinal axis of the electrode lead at a point adjacent the electrode tip. Also, certain prior art devices have employed means to hold the tines against the electrode lead during insertion in an attempt to reduce the resistance to passage through blood vessels. The tines are then released when the distal tip is properly positioned in the heart.

A primary disadvantage of such prior art arrangements stems from the abrupt transitions created at the base of the tines when they are in a folded configuration. Such abrupt transitions are a source of trauma to the inside walls of blood vessels, cause increased resistance to passage of the electrode lead through the vessels, and hence limit the minimum size blood vessel through which the electrode leads may pass.

A new approach to the designing of an anchoring means is set forth in U.S. patent application Ser. No. 114,950 filed Jan. 23, 1980, on behalf of Carl Doring and entitled "Trailing Tine Electrode Lead." The trailing tine electrode lead described therein comprises an exposed conductive distal tip, a conductive shank supporting the distal tip, an electrical conductor coupled to a proximal end of the shank, and an insulating covering over the shank and the conductor. The insulating cover includes a transitional section having a proximal end, and a plurality of flexible tines connected to the insulating cover at and trailing behind the proximal end of the transitional section. The tines are flexible and fold backward along sides of the conductor of the electrode lead upon encountering an obstacle, such as the inside wall of a vein, during insertion. When folded, the tines present a minimized cross-sectional area equal to the sum of the cross-sectional area of the tines and the cross-sectional area of the insulated conductor.

Despite the marked advantages of the trailing tine design, it would be desirable to further minimize the cross-sectional area of the electrode lead in order to facilitate further the insertion and removal of the lead and to minimize trauma to blood vessels as the lead passes therethrough.

OBJECTS AND SUMMARY OF THE INVENTION

Accordingly, it is an object of the present invention to minimize the cross-sectional area of an electrode lead.

Another object of this invention is to eliminate substantially any increase in the cross-sectional area of an electrode lead that is due to the provision of anchoring means on the lead.

Still another object of this invention is to facilitate the passage of electrode leads through blood vessels by providing a substantially smooth exterior surface for the leads.

Yet another object of this invention is to minimize trauma to blood vessels when inserting and removing electrode leads.

Additional objects and advantages of the invention will be set forth in part in the description which follows, and in part will be apparent from the description or may be learned from the practice of the invention. The objects and advantages of the invention may be realized and obtained by means of the instrumentalities and combinations particularly pointed out in the appended claims.

To achieve the foregoing objects in accordance with the invention, as embodied and broadly described herein, an electrode lead for implant into a heart comprises an electrical conductor, an insulative sheath covering a portion of the electrical conductor and having a proximal end and a distal end, an electrode tip electrically coupled to an uninsulated portion of the electrical conductor, and means for joining the insulative sheath to the electrode tip by forming a first lap joint with the proximal end of the electrode tip and a second lap joint with the distal end of the insulative sheath.

In a preferred embodiment, the joining means further includes foldable anchoring means extending from the first lap joint toward the second lap joint and a recessed portion intermediate the first lap joint and the second lap joint for receiving the anchoring means when folded to be substantially flush with the exterior surface of the first and second lap joints to minimize the diameter of the electrode lead.

BRIEF DESCRIPTION OF THE DRAWINGS

A greater appreciation of the objects and the advantages of the present invention can best be understood in light of the following detailed description when considered in conjunction with the accompanying drawings, in which:

FIG. 4 is a cross-sectional view of a bipolar embodiment of the electrode lead of the present invention.

DETAILED DESCRIPTION OF THE PREFERRED EMBODIMENT

Figure 1:
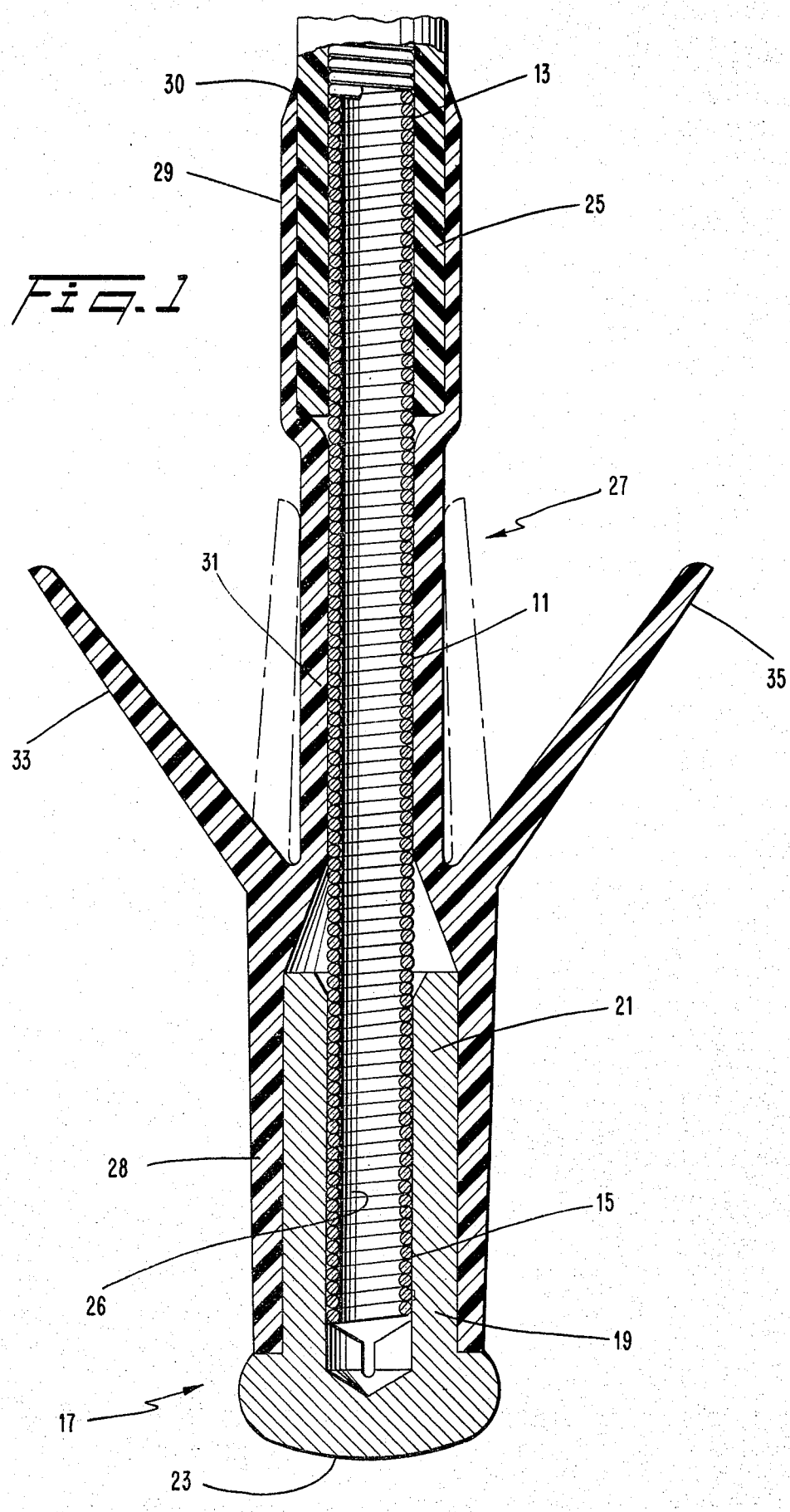
FIG. 1 is a cross-sectional view of a unipolar embodiment of the electrode lead of the present invention.

Referring to FIG. 1, the electrode lead comprises an electrical conductor 11 having a proximal end 13 and a distal end 15. The electrical conductor 11 is designed to interconnect pacemaker circuitry (not shown) with an electrode tip 17. As referred to in this description, the term "proximal" always refers to the end of an element closest to the pacemaker circuitry wherein the term "distal" refers to the end of an element closest to the electrode tip 17.

The electrode tip 17 includes a shank portion 19 having a proximal end 21 and a distal end 23.

The electrical conductor 11 is typically a helically wound wire or plurality of interwound wires which is known in the art as a "helix." The helix exhibits flexibility, conductivity, and strength. The electrode tip 17 is typically supported by the conductive shank 19 which has an axial opening 26 at its proximal end 21 to receive the distal end 15 of the electrical conductor 11. The electrical conductor is covered by an insulative sheath 25 of, for example, polyurethane. The outside diameter of the insulative sheath 25 measures 4F wherein the unit F indicates the French gauge and corresponds to three times the outside diameter of the insulative sheath 25 in millimeters.

Figure 2:
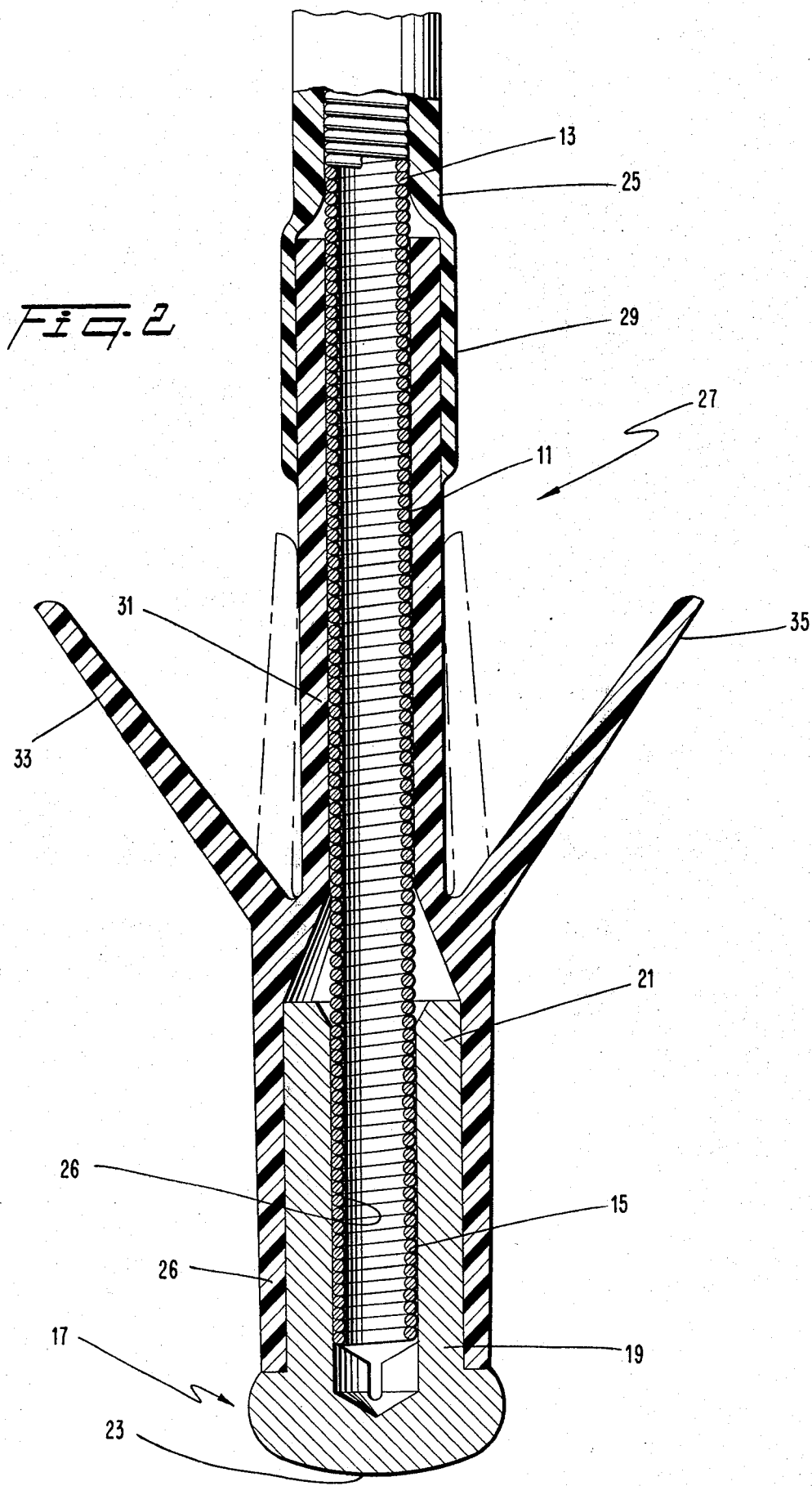
FIGS. 2 and 3 are cross-sectional views of two further unipolar embodiments of the electrode lead of the present invention.
Figure 3:
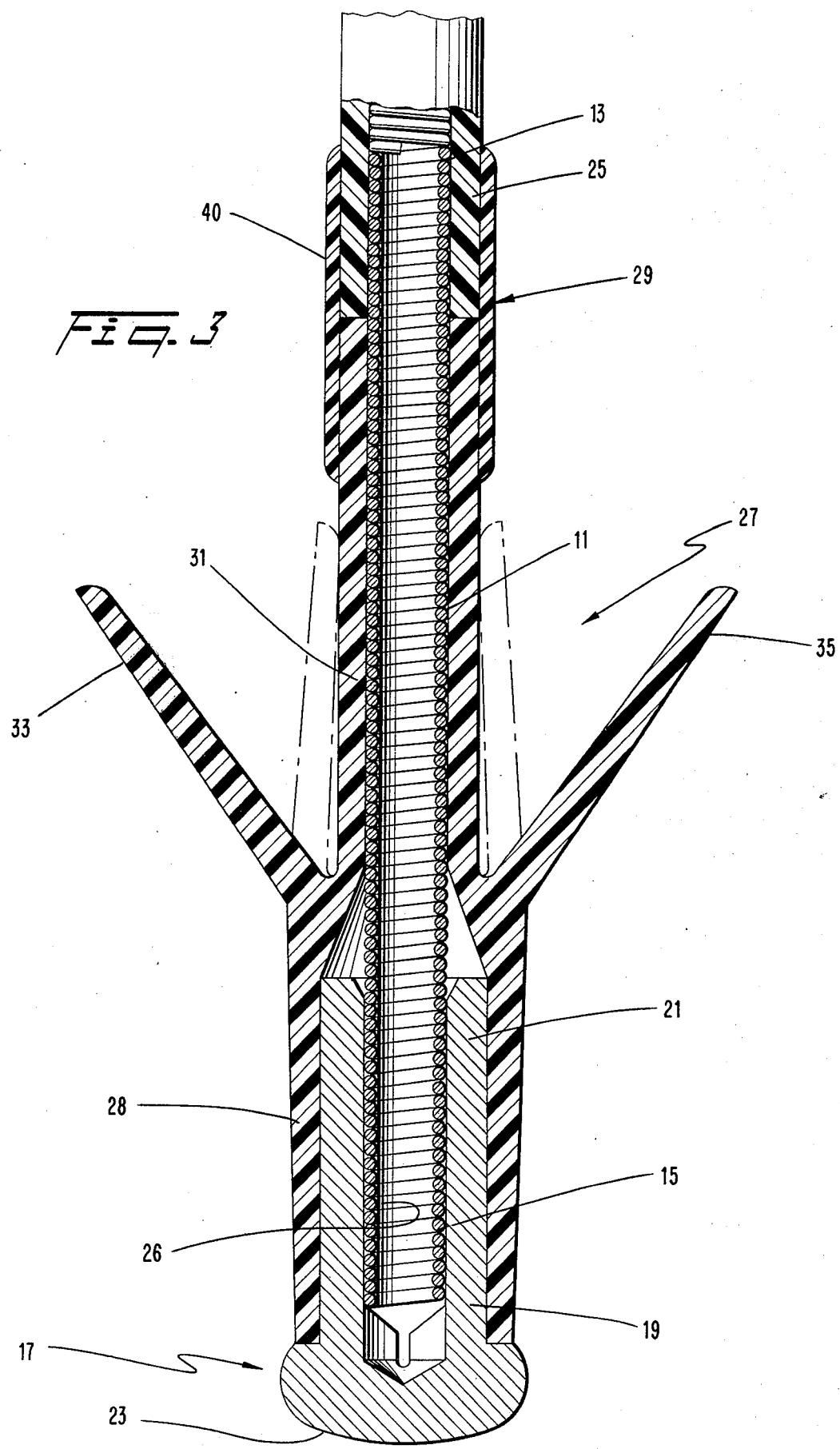

As embodied herein, the joining means comprises a molding member 27, preferably composed of insulative material, forming a first lap joint 28 with the shank 19 of the electrode tip 17, and a second lap joint 29 with the distal end of the insulative sheath 25 surrounding the electrical conductor 11. In FIG. 1, the proximal end of the molding overlaps the distal end of the insulating sheath. The same effect could be achieved by overlapping the distal end of the insulating sheath over the proximal end of the molding as shown in FIG. 2. As a further alternative, shown in FIG. 3, a joining tube 40 could be provided which overlaps both the distal end of the insulating sheath 25 and the proximal end of the molding member 27. In each case, the molding member 27 also includes a recessed portion 31 intermediate the first lap joint 28 and the second lap joint 29.

In accordance with the present invention, the means for anchoring comprises a plurality of resilient or flexible tines 33, 35. The tines 33, 35 are, for example, formed integrally with the molding member 27 and have base portions extending from the proximal end of the first lap joint 28. The tines 33, 35 extend from the base portion in a trailing relationship behind the proximal end of the first lap joint 28.

By being attached to the proximal end of the first lap joint 28, the tines 33, 35 do not present an abrupt transition to obstacles when folded. The recessed portion 31 of the molding 27 receives the tines 33, 35 when they are in a folded position (as seen in phantom in FIGS. 1 and 2). When folded, the tines 33, 35 do not add substantially to the cross-sectional area of the electrode lead.

Because the trailing tines 33, 35 in this invention fold flat against the molding 27 at the recessed portion 31, the tines 33, 35, when folded, present a smaller cross-sectional width than equivalent thickness tines of the prior art. Accordingly, the electrode lead structure illustrated in FIG. 1 facilitates insertion while retaining the anchoring benefits of prior art tined electrodes. In addition, during withdrawal or repositioning in a tight vein the tips of the tines 33, 35 will not protrude due to recessed portion 31 and are less likely to snag or cause trauma.

The design of the molding member 27 also results in the electrode leads having a smooth, uniform exterior surface. As illustrated in FIG. 1, the distal end of the first lap joint 28 is tucked behind the distal end 23 of the electrode tip 17. When the tines 33, 35 are folded into the recessed portion 31 of the molding member 27, a substantially smooth, uniform-diameter surface is presented along the entire length of the molding member 27 extending from the distal end of the first lap joint 28 to a tapered portion 30 at the proximal end of the second lap joint 29.

The utilization of the lap joint 29 to connect the distal end of the insulative sheath 25 to the proximal end of the molding member 27 provides the additional advantage of strengthening the joint.

In the past, the electrical conductor has been covered by a first insulative sheath and the electrode tip has been covered by a second insulative sheath. In most designs, the sheaths have been glued together at a butt joint. Necessarily, the glue can be provided on only a small area, i.e., the cross-sectional area of the respective insulative sheaths. For an insulative sheath having a 0.25 mm wall thickness and a 1.3 mean diameter, the entire glue area approximated 1 mm². Thus, any tension applied to the electrode lead necessarily bore upon the small butt joint between the two insulative sheaths resulting in an increased risk of failure. Moreover, the cut ends of the insulative sheaths to be joined but butt joints must be absolutely square or perpendicular to the longitudinal axes of the sheaths and the glue must be well placed in order to avoid gaps in the butt joint that would enable fluid to enter the electrode lead and further weaken the joint.

In contrast, the utilization of the lapped joint 29 gives good mating between the exterior surface of the distal end of the insulative sheath 25 and the interior surface of the proximal end of the molding member 27. Glue can be loaded in shear along the entire length of the second lap joint 29. The chance of a gap occurring in the lap joint 29 is thus minimized. If, for example, the second lap joint 29 extends for 2.5 mm, the total glue area will approximate 10 mm², thereby spreading any tensions bearing upon the lap joint 29 across a far greater surface area than in the butt joint structure of the prior art. The utilization of lap joint 29 increases the strength of the electrode lead and reduces the likelihood that fluids will penetrate the joint and enter the electrode lead.

The positioning of lap joints 28 and 29 to connect the distal end of the insulative sheath 25 to the proximal end 21 of the electrode tip 17 also provides a structure which decreases the cross-sectional diameter of the lead.

A previous design as set forth in the previously referenced patent application included a lap joint positioned coincident with the base of the tines. Thus, necessarily the cross-sectional area of the lead was increased as a result of the two layers of insulative material under the base of the tines.

In contrast, the positioning of lap joint 29 beyond the folded position of the tines 33 results in a smaller uniform cross-sectional diameter for the lead as only one layer of insulative material lies beneath the tines.

FIG. 1 illustrates the embodiment of the present invention constructed as a unipolar electrode lead. FIG. 4 illustrates an embodiment of the instant invention with a bipolar electrode lead with an indifferent electrode ring 37 being provided just above the proximal end of the second lap joint 29. In such a bipolar embodiment, a second electrical conductor 39 is provided coaxially with the electrical conductor 11 and is coupled to the electrode ring 37. Elements common to the embodiments of the present invention for unipolar and bipolar leads are designated by like reference numerals in FIG. 1 and FIG. 4. It will be apparent that the advantages of the instant invention resulting from its use with a unipolar lead are equally achievable when the electrode lead is bipolar.

It will be apparent, to those skilled in the art, that modifications and variations can be made in the preferred embodiment disclosed herein and in the method of constructing the preferred embodiment without departing from the scope or the spirit of the invention. Thus, it is intended that the present invention include those modifications and variations which come within the scope of the appended claims and their equivalents.

What is claimed is:

1. An electrode lead for implant into a heart comprising:
   a first electrical conductor having a distal end and a proximal end;
   a first electrode connected to the distal end of said first conductor, said first electrode having an exposed distal tip and a proximal shank;
   a first insulative sheath covering a portion of said first electrical conductor extending from said proximal end thereof toward said distal end;
   flexible, insulative joining means having a distal end overlapping said proximal shank of said first electrode to form a first elongated lap joint, a proximal end connected to the distal end of said first insulative sheath to form a second elongated lap joint, and a recessed portion intermediate said first and second lap joints; and
   foldable anchoring means attached to said joining means in the vicinity of the transition between said first lap joint and said recessed portion, said anchoring means when in a relaxed, unfolded state extending angularly from said joining means and adapted to engage heart tissue upon implant and when folded being received into said recessed portion to minimize the diameter of said electrode lead.

2. An electrode lead in accordance with claim 1 wherein said anchoring means when folded lie substantially flush with the exterior surface of said first and second lap joints.

3. An electrode lead in accordance with claim 1 wherein said anchoring means includes a plurality of non-conductive resilient tines.

4. An electrode lead in accordance with claim 1, 2, or 3 wherein said second lap joint is formed by the proximal end of said joining means overlapping the distal end of said first insulative sheath.

5. An electrode lead in accordance with claim 1, 2, or 3 wherein said second lap joint is formed by the distal end of said first insulative sheath overlapping the proximal end of said joining means.

6. An electrode lead in accordance with claim 1, 2, or 3 wherein said second lap joint is formed by means of a lap joint member which overlaps both the proximal end of said joining means and the distal end of said first insulative sheath.

7. An electrode lead in accordance with claim 1, 2, or 3 wherein said anchoring means and said joining means are molded integrally.

8. An electrode lead in accordance with claim 1, 2, or 3 wherein said anchoring means and said joining means are made of silicone elastomer material.

9. An electrode lead in accordance with claim 1, 2, or 3 wherein said anchoring means and said joining means are made of polyurethane material.

10. An electrode lead in accordance with claim 1, 2, or 3 wherein said first insulative sheath is made of silicone elastomer material.

11. An electrode lead in accordance with claim 1, 2, or 3 wherein said first insulative sheath is made of polyurethane material.

12. An electrode lead in accordance with claim 1, 2, or 3 wherein said distal tip of said first electrode, said first lap joint, and said folded anchoring means are all of substantially equal outside diameter.

13. An electrode lead in accordance with claim 1, 2, or 3 which further includes a second electrical conductor electrically insulated from said first electrical conductor, a second insulative sheath covering said second electrical conductor, and a second electrode connected to the distal end of said second electrical conductor, said second electrode being positioned proximally to said second lap joint.

14. An electrode lead in accordance with claim 13 in which said second electrode is adjacent to the proximal end of said second lap joint.

15. An electrode lead in accordance with claim 14 wherein said second insulative sheath, said second electrode, said second lap joint, said folded anchoring means, and said first lap joint are all of substantially equal outside diameter.

16. An electrode lead in accordance with claim 14 wherein said second insulative sheath, said second electrode, said second lap joint, said folded anchoring means, and said first lap joint are adapted to present a substantially smooth and continuous external surface.

17. An electrode lead in accordance with claim 6 further including a second electrical conductor electrically insulated from said first electrical conductor, a second insulative sheath covering said second electrical conductor, and a second electrode connected to the distal end of said second electrical conductor, said second electrode being positioned proximally to said second lap joint, said lap joint member being extended proximally to abut said second electrode.

18. An electrode lead in accordance with claim 17 in which said second insulative sheath, said second electrode, said lap joint member, said folded anchoring means, and said first lap joint are all of substantially equal outside diameter.

19. An electrode lead in accordance with claim 17 in which said second insulative sheath, said second electrode, said lap joint member, said folded anchoring means, and said first lap joint are adapted to present a substantially smooth continuous external surface.

* * * * *